United States Patent [19]

Clauson-Kaas et al.

[11] 4,454,318
[45] * Jun. 12, 1984

[54] METHOD FOR PRODUCING 4-CHLORO-5-AMINO-2-PHENYL-3(2H)-PYRIDAZINONE FROM 4,5-DICHLORO-2-PHENYL-3(2H)-PYRIDAZIONE AND AMMONIA

[75] Inventors: Niels Clauson-Kaas, Copenhagen; Gert Jansen, Forum; Erik Olsen, Køge, all of Denmark

[73] Assignee: BASF Aktiengesellschaft, Fed. Rep. of Germany

[*] Notice: The portion of the term of this patent subsequent to Oct. 27, 1998 has been disclaimed.

[21] Appl. No.: 253,840
[22] PCT Filed: Oct. 17, 1980
[86] PCT No.: PCT/DK80/00062
§ 371 Date: Apr. 16, 1981
§ 102(e) Date: Apr. 16, 1981
[87] PCT Pub. No.: WO81/01288
PCT Pub. Date: May 14, 1981

[30] Foreign Application Priority Data

Oct. 31, 1979 [DK] Denmark .............................. 4613/79

[51] Int. Cl.$^3$ .................... C07D 237/22; C07D 237/14
[52] U.S. Cl. .................................................... 544/241
[58] Field of Search .......................................... 544/741

[56] References Cited

U.S. PATENT DOCUMENTS 4,297,493 10/1981 Richarz et al. ...................... 544/241

OTHER PUBLICATIONS

Szabo, Chem. Abs. 86, 72686b (1976).

Primary Examiner—Mark L. Berch
Attorney, Agent, or Firm—Keil & Witherspoon

[57] ABSTRACT

4-Chloro-5-amino-2-phenyl-3(2H)-pyridazinone is prepared from 4,5-dichloro-2-phenyl-3(2H)-pyridazinone and ammonia in high yield and substantially free from 4-amino-5-chloro-2-phenyl-3(2 H)-pyridazinone in a method comprising reacting 4,5-dichloro-2-phenyl-3(2H)-pyridazinone with aqueous ammonia in the presence of a catalyst which is capable of selectively exchanging the 5-chlorine atom in 4,5-dichloro-2-phenyl-3(2H)-pyridazinone with a leaving group of such a nature that the resulting intermediate compound is capable of alkylating ammonia to 4-chloro-5-amino-2-phenyl-3(2H)-pyridazinone in high yield in the reaction medium, thereby regenerating the catalyst. The end product is isolated by filtration after the reaction and washed with water, and the mother liquor plus the wash water are used as reaction medium for the next batch.

4 Claims, No Drawings

METHOD FOR PRODUCING 4-CHLORO-5-AMINO-2-PHENYL-3(2H)-PYRIDAZINONE FROM 4,5-DICHLORO-2-PHENYL-3(2H)-PYRIDAZIONE AND AMMONIA

The present invention relates to a method for producing 4-chloro-5-amino-2-phenyl-3(2H)-pyridazinone from 4,5-dichloro-2-phenyl-3(2H)-pyridazinone and ammonia.

4-Chloro-5-amino-2-phenyl-3(2H)-pyridazinone is a selectively acting herbicide, especially for the use in sugar beet areas. Sugar beets show specific resistance against this compound. 4-Chloro-5-amino-2-phenyl-3(2H)-pyridazinone has hitherto been produced from mucochloric acid via reaction with phenyl hydrazine for the preparation of the dichloropyridazinone derivative (4,5-dichloro-2-phenyl-3(2H)-pyridazinone) which is thereafter reacted with ammonia under pressure and at elevated temperature for the preparation of the desired 4-chloro-5-amino-2-phenyl-3(2H)-pyridazinone. In this last reaction step, about 10–20% of the isomeric compound, 4-amino-5-chloro-2-phenyl-3(2H)-pyridazinone, which has only half the herbicidal effect of 4-chloro-5-amino-2-phenyl-3(2H)-pyridazinone, is produced.

German Pat. No. 1,105,232 discloses the preparation of 4-chloro-5-amino-2-phenyl-3(2H)-pyridazinone from 4,5-dichloro-2-phenyl-3(2H)-pyridazinone and ammonia. 4-Chloro-5-amino-2-phenyl-3(2H)-pyridazinone is isolated in a 64% yield from the reaction product together with a 10% yield of the isomeric product.

German Offenlegungsschrift No. 2,100,685 states that the crude reaction product from the reaction described in German Pat. No. 1,105,232 contains 80% of 4-chloro-5-amino-2-phenyl-3(2H)-pyridazinone and 20% of the isomeric compound and gives directions for isolating pure 4-chloro-5-amino-2-phenyl-3(2H)-pyridazinone from this mixture by extraction with certain solvents.

Czechoslovakian Pat. No. 158,843 discloses the preparation of 4-chloro-5-amino-2-phenyl-3(2H)-pyridazinone by passing ammonia into molten 4,5-dichloro-2-phenyl-3(2H)-pyridazinone at 208°–220° C. A 93% pure product is obtained in a 71% yield.

No way of carrying out the reaction of 4,5-dichloro-2-phenyl-3(2H)-pyridazinone with ammonia giving pure 4-chloro-5-amino-2-phenyl-3(2H)-pyridazinone in high yield is known.

The present invention provides a method by which 4-chloro-5-amino-2-phenyl-3(2H)-pyridazinone is produced in high yield and substantially free from 4-amino-5-chloro-2-phenyl-3(2H)-pyridazinone. The method of the invention comprises reacting 4,5-dichloro-2-phenyl-3(2H)-pyridazinone with aqueous ammonia in the presence of a catalyst which is capable of selectively exchanging the 5-chlorine atom in 4,5-dichloro-2-phenyl-3(2H)-pyridazinone with a leaving group of such a nature that the resulting intermediate compound is capable of alkylating ammonia to 4-chloro-5-amino-2-phenyl-3(2H)-pyridazinone in high yield in the reaction medium, thereby regenerating the catalyst. A type of catalysts are such compounds which form an intermediate compound which is soluble or dispersible in the reaction medium. In one aspect of the invention, the catalyst is such an organic compound that the intermediate compound has a melting point below the reaction temperature.

One type of catalysts is constituted by phenolic compounds which make the intermediate compound water-soluble. Examples of such phenolic compounds are 3-hydroxy-2-pyridone and 3-hydroxypyridine and phenol derivatives containing a water-solubility-imparting substituent group such as a sulphonic acid group or a carboxylic acid group, e.g. 4-hydroxyphenyl acetic acid, 4-hydroxy-benzoic acid, 1-phenol-4-sulphonic acid and 1-naphthol-5-sulphonic acid. These catalysts clearly illustrate the invention which, however, in no way shall be limited to the use of only the above-mentioned catalysts, all other catalysts complying with the above criteria being equally suitable.

The ratio between the starting material 4,5-dichloro-2-phenyl-3(2H)-pyridazone and the catalyst is from 50:1 to 2:1, calculated on molar basis.

The reaction involves the use of 1 mole of ammonia per mole of 4,5-dichloro-2-phenyl-3(2H)-pyridazinone and 1 mole of an alkaline agent neutralizing the HCl formed; hence, it is suitable to employ at least 2 mole of ammonia per mole of 4,5-dichloro-2-phenyl-3(2H)-pyridazinone, and the molar ratio between ammonia and the starting material may be in the range of 2.1:1 to 10:1.

The ammonia may be used as a concentrated, aqueous solution, or as a more dilute aqueous solution.

The method according to the invention may be carried out in a closed vessel, at moderate pressures, and at temperatures between about 50° C. and 150° C. with stirring.

At the beginning of the reaction, the reaction mixture is a slurry of 4,5-dichloro-2-phenyl-3(2H)-pyridazinone, and at the end of the reaction, the reaction mixture is a slurry of the 4-chloro-5-amino-2-phenyl-3(2H)-pyridazinone formed. During the reaction, part of the reactants are soluble or dispersible in the reaction medium.

The end product is isolated by filtration after the reaction, washed with water and dried.

One aspect of the present invention is to provide a simple "one pot" method, in which the reaction solution containing ammonia and catalyst, after isolation of the 4-chloro-5-amino-2-phenyl-3(2H)-pyridazinone, may be reused a number of times. In this aspect, the mother liquor plus the wash water are used as reaction medium for the next batch after isolation of the product by filtration. Thereby the catalyst is reused, and the loss of 4-chloro-5-amino-2-phenyl-3(2H)-pyridazinone caused by its solubility in the reaction medium, is reduced.

It is preferred that the amount of reaction medium retained in the filter cake be replaced by a corresponding amount of wash water and fed back to the reaction medium.

The method according to the invention is illustrated in the following examples:

EXAMPLE 1

4,5-Dichloro-2-phenyl-pyridazinone (2.41 g), 4-hydroxyphenyl-acetic acid (1.0 g) and 20% aqueous ammonia (20 ml) were heated to 100°–110° C. with stirring in a small autoclave for 4 hours. The reaction mixture was then cooled to room temperature, and the resulting precipitate of 4-chloro-5-amino-2-phenyl-3(2H)-pyridazinone was isolated by filtration, washed with water and dried. 1.86 g of pure 4-chloro-5-amino-2-phenyl-3(2H)-pyridazinone were obtained, m.p. 206°–207° C. The mother liquor and the washings contained 0.15 g of 4-chloro-5-amino-2-phenyl-3(2H)- pyridazinone. The total amount of 4-chloro-5-amino-2-phenyl-3(2H)-pyridazinone formed was thus 2.01 g (91%).

EXAMPLE 2

4,5-Dichloro-2-phenyl-pyridazinone (12.0 g), 4-hydroxy-benzoic acid (3.5 g), water (75 ml) and 20% aqueous ammonia (25 ml) were heated to 145°–150° C. with stirring in a glass autoclave for 5 hours.

The reaction mixture was then cooled to room temperature, and the resulting precipitate of 4-chloro-5-amino-2-phenyl-3(2H)-pyridazinone was isolated by filtration, washed with water (100 ml) and dried. 9.3 g of 4-chloro-5-amino-2-phenyl-3(2H)-pyridazinone were thereby obtained, while 0.8 g of 4-chloro-5-amino-2-phenyl-3(2H)-pyridazinone remained dissolved in the mother liquor and washings. The total amount of 4-chloro-5-amino-2-phenyl-3(2H)-pyridazinone formed was thus 10.1 g (91%).

EXAMPLE 3

Example 2 was repeated, using 1-phenol-4-sulphonic acid (4.4 g) instead of 4-hydroxy-benzoic acid. 9.6 g of 4-chloro-5-amino-2-phenyl-3(2H)-pyridazinone were obtained while 0.8 g remained dissolved in the mother liquor and washings. In all, 10.4 g (94%) of 4-chloro-5-amino-2-phenyl-3-(2H)-pyridazinone were thus formed.

EXAMPLE 4

Example 2 was repeated, using the following catalysts instead of 4-hydroxy-benzoic acid: (A) 3-hydroxy-2-pyridone (2.7 g), (B) 3-hydroxy-pyridine (2.4 g), and (C) 1-naphthol-5-sulphonic acid (5.6 g).

EXAMPLE 5

Example 3 was repeated using instead of a molar ratio of starting material and catalyst of 2:1 a molar ratio of 10:1 corresponding to 0.9 g of 1-phenyl-4-sulphonic acid instead of 4.4 g.

The resulting samples of 4-chloro-5-amino-2-phenyl-3(2H)-pyridazinone from Examples 2, 3, 4 and 5 were analysed (m.p. and G.L.C.). The results are shown in Table I.

TABLE I

| Example | M.p. | G.L.C. analysis, % | | |
|---|---|---|---|---|
| | | Starting compound | Isomeric compound | Desired compound |
| 2 | 207-8 | 0.2 | 0.1 | 99.7 |
| 3 | 208-9 | 0.3 | 0.1 | 99.6 |
| 4 A | 208 | 0.0 | 0.0 | 100.0 |
| 4 B | 207-8 | 0.1 | 0.3 | 99.6 |
| 4 C | 207-8 | 0.5 | 0.1 | 98.4 |
| 5 | 205-6 | 0.5 | 1.7 | 97.2 |

EXAMPLE 6

Example 3 was repeated using different molar ratios of starting material and catalyst. The results are shown in Table II.

TABLE II

| Molar ratio Start.mat.:cat. | G.L.C. analysis, % | | |
|---|---|---|---|
| | Starting compound | Isomeric compound | Desired compound |
| 2:1 | 0.3 | 0.1 | 99.6 |
| 4:1 | 0.8 | 1.4 | 96.3 |
| 8:1 | 0.7 | 3.7 | 94.5 |
| 8:1 | 1.4 | 4.2 | 91.7 |
| 8:1 | 0.8 | 3.8 | 94.1 |

We claim:
1. A method for producing 4-chloro-5-amino-2-phenyl-3(2H)-pyridazinone from 4,5-dichloro-2-phenyl-3(2H)-pyridazinone and ammonia in high yield and substantially free from 4-amino-5-chloro-2-phenyl-3(2H)-pyridazinone with aqueous ammonia in the presence of a catalyst which is capable of selectively exchanging the 5-chlorine atom in 4,5-dichloro-2-phenyl-3(2H)-pyridazinone with a leaving group of such a nature that the resulting intermediate compound is capable of alkylating ammonia to 4-chloro-5-amino-2-phenyl-3(2H)-pyridazinone in high yield in the reaction medium, thereby regenerating the catalyst, said catalyst being selected from the group consisting of 4-hydroxyphenyl-acetic acid, 4-hydroxy-benzoic acid, 3-hydroxy-2-pyridone, and 3-hydroxy-pyridine.

2. The method of claim 1 in which the ratio between 4,5-dichloro-2-phenyl-3(2H)-pyridazinone and the catalyst is from 50:1 to 2:1, calculated on a molar basis.

3. The method of claim 1 or 2 in which the molar ratio between ammonia and the starting material is 2.1:1–10:1.

4. The method of claim 2 in which the end product is isolated by filtration at room temperature after the reaction and washed with water, and the mother liquor plus the wash water are used as the reaction medium for the next batch.

* * * * *

UNITED STATES PATENT AND TRADEMARK OFFICE
CERTIFICATE OF CORRECTION

PATENT NO. : 4,454,318
DATED : June 12, 1984
INVENTOR(S) : Clauson-Kaas et al.

It is certified that error appears in the above-identified patent and that said Letters Patent is hereby corrected as shown below:

IN THE TITLE:

Third to last word "PYRIDAZIONE" should read --PYRIDAZINONE--.

Signed and Sealed this

Twenty-ninth Day of October 1985

[SEAL]

Attest:

Attesting Officer

DONALD J. QUIGG

Commissioner of Patents and
Trademarks—Designate